(12) United States Patent
Thome et al.

(10) Patent No.: US 10,743,799 B2
(45) Date of Patent: Aug. 18, 2020

(54) MEDICAL INSTRUMENT WITH A SHUTTER FOR SEALING A TEST STRIP PORT

(71) Applicant: Roche Diagnostics Operations, Inc., Indianapolis, IN (US)

(72) Inventors: Klaus Thome, St. Leon-Rot (DE); Reiner Stein, Bad Kreuznach (DE); Lars Fischheiter, Ludwigsburg (DE); Jerome Greenhalgh, Kornwestheim (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 375 days.

(21) Appl. No.: 15/746,991

(22) PCT Filed: Jul. 29, 2016

(86) PCT No.: PCT/EP2016/068241
§ 371 (c)(1),
(2) Date: Jan. 23, 2018

(87) PCT Pub. No.: WO2017/017275
PCT Pub. Date: Feb. 2, 2017

(65) Prior Publication Data
US 2018/0206768 A1    Jul. 26, 2018

(30) Foreign Application Priority Data
Jul. 29, 2015   (EP) .................................... 15178860

(51) Int. Cl.
*A61B 5/145* (2006.01)
*G01N 33/487* (2006.01)
*G01N 35/00* (2006.01)

(52) U.S. Cl.
CPC ..... *A61B 5/14532* (2013.01); *G01N 33/4875* (2013.01); *G01N 35/00029* (2013.01);
(Continued)

(58) Field of Classification Search
CPC .......... A61B 5/14532; A61B 2562/247; A61B 2560/0443; A61B 2562/0295;
(Continued)

(56) References Cited

U.S. PATENT DOCUMENTS

| 8,158,081 B2 | 4/2012 | Scott et al. |
| 2010/0249567 A1 | 9/2010 | Harttig et al. |

(Continued)

FOREIGN PATENT DOCUMENTS

| CN | 101227859 A | 7/2008 |
| EP | 2741076 A1 | 6/2014 |

(Continued)

OTHER PUBLICATIONS

International Search Report and Written Opinion dated Oct. 24, 2016 for PCT/EP2016/068241 Filed Jul. 29, 2016. pp. 1-12.
(Continued)

*Primary Examiner* — Dennis White
(74) *Attorney, Agent, or Firm* — Dinsmore & Shohl, LLP

(57) ABSTRACT

A medical instrument (300, 700, 1300, 1400, 1500, 1600) for performing a measurement (1513) on a biological sample using a test strip (310), wherein the medical instrument comprises: a housing (302) and an analytical unit (1508) for analyzing the test strip, wherein the analytical unit is within an interior volume (308). The analytical unit comprises a test strip mount (1510) configured for receiving the test strip to perform the measurement. The instrument further comprises a test strip port (312) between an exterior surface (304) and an interior surface (306). The test strip port is aligned with the test strip mount along an insertion direction (328). The medical instrument further comprises a shutter (100) for sealing the test port. The shutter is configured for being in a open position and a closed position. The shutter is within the interior volume. The shutter is configured for sealing the test
(Continued)

port when in the closed position. The shutter comprises a test strip opening (106). The test strip opening is aligned with the test strip port and the test strip mount when the shutter is in the open position. The shutter has a first sealing surface (118). The test strip port has a second sealing surface (120). The first sealing surface and the second sealing surface are configured to mate in the closed position. The shutter comprises a mechanism for moving the shutter between the open position and the closed position. Moving the shutter between the closed position and the open position comprises a rotation of the shutter parallel to the insertion direction. The medical instrument further comprises an actuator (2506) for actuating the mechanism to move the shutter between the open position and the closed position.

20 Claims, 11 Drawing Sheets

(52) U.S. Cl.
CPC .................. *A61B 2560/0443* (2013.01); *A61B 2562/0295* (2013.01); *A61B 2562/247* (2013.01); *G01N 35/00722* (2013.01); *G01N 2035/0091* (2013.01)

(58) Field of Classification Search
CPC ......... G01N 35/00029; G01N 33/4875; G01N 2035/0091; G01N 35/00722
See application file for complete search history.

(56) References Cited

U.S. PATENT DOCUMENTS

| 2012/0150448 A1 | 6/2012 | Hurd et al. |
| 2014/0123735 A1* | 5/2014 | Uenosono ............. G01N 33/49 73/61.41 |

FOREIGN PATENT DOCUMENTS

| WO | 2007010087 A1 | 1/2007 |
| WO | 2010024971 A1 | 3/2010 |
| WO | 2014172831 A1 | 10/2014 |

OTHER PUBLICATIONS

International Preliminary Report on Patentability dated Jan. 30, 2018 for PCT/EP2016/068241 Filed Jul. 29, 2016. pp. 1-6.
ACCU-CHEK Inform II Blood Glucose Monitoring Systems Operator's Manual, Version 3.0 (Roche Diagnostics GmbH, Mannheim, Germany, Mar. 2013, http://www.accu-chekinformii.com/pdf/05234646002_ACI2_OpsMan.pdf.
Chinese Office Action dated Jan. 3, 2020 in co-pending Chinese Application No. 201680042637.4.

* cited by examiner

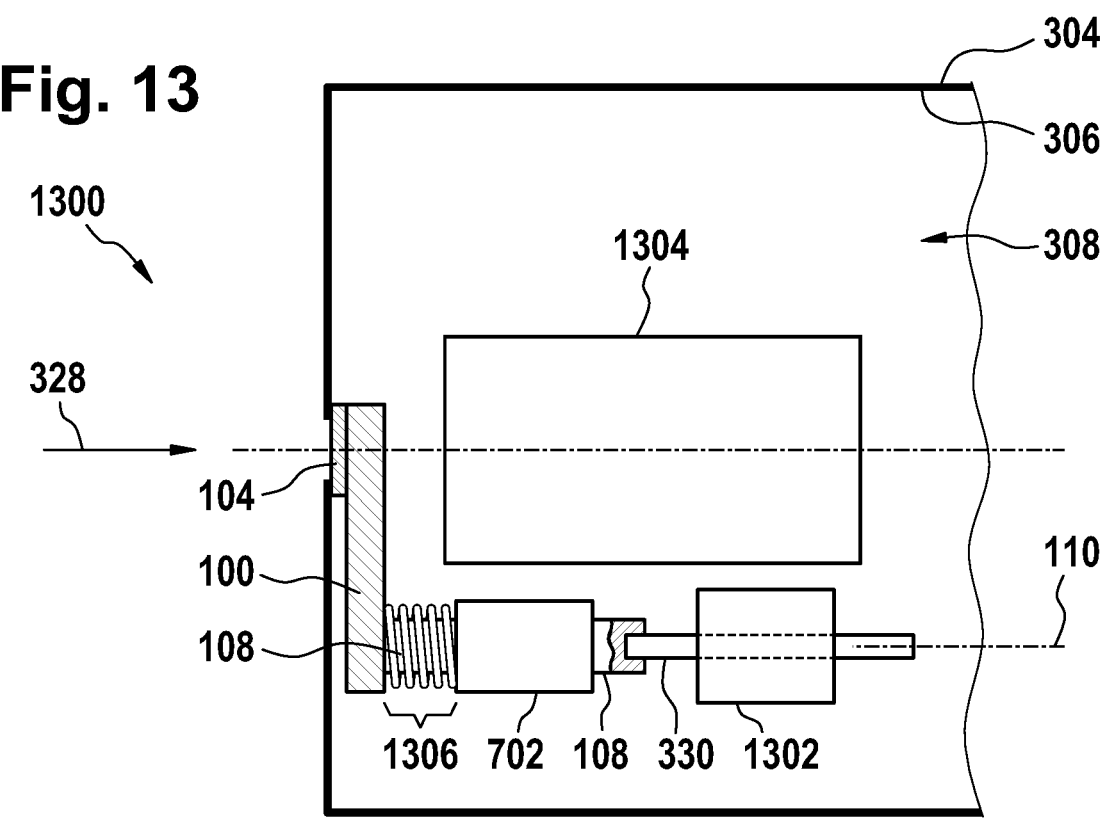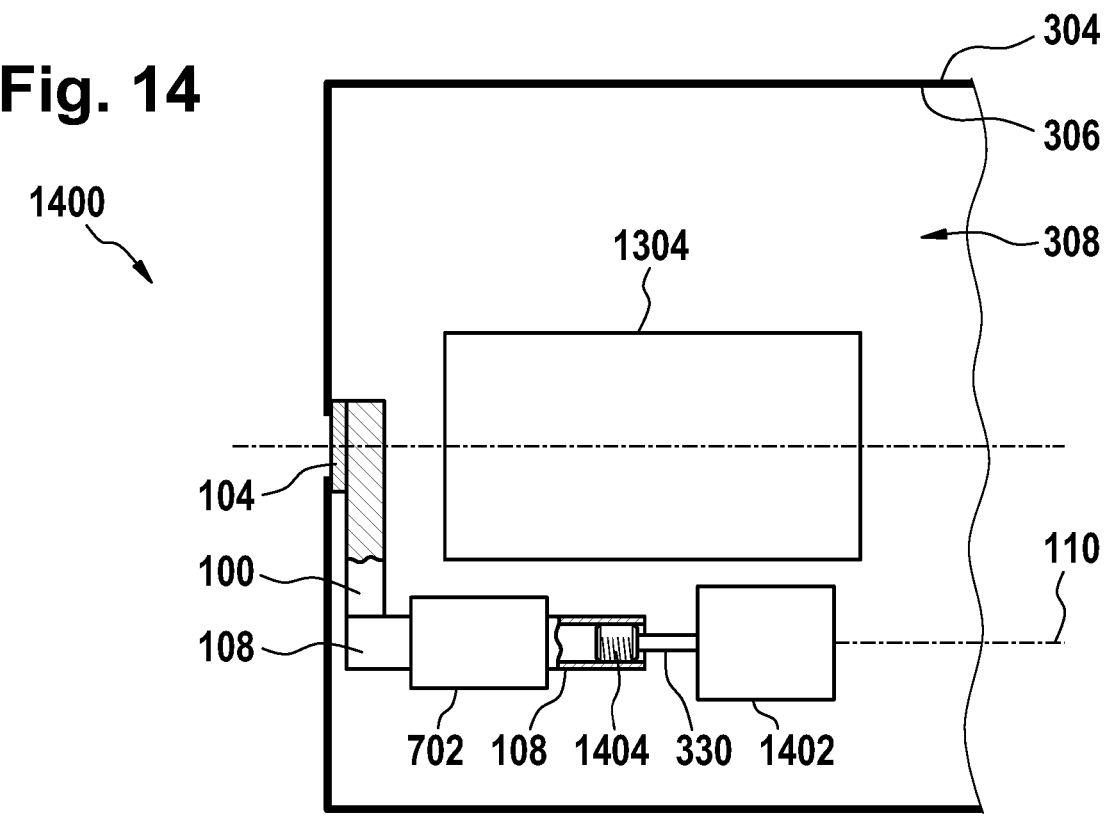

MEDICAL INSTRUMENT WITH A SHUTTER FOR SEALING A TEST STRIP PORT

FIELD OF THE INVENTION

The invention relates to medical instruments and methods of operating medical instruments, in particular to the cleaning and disinfection of test strip ports of analyzers

BACKGROUND AND RELATED ART

In hospitals and other clinical settings, healthcare providers may use medical instruments such as test strip readers or analyte monitoring devices to perform diagnostic tests on multiple patients. Current infection control protocols require that the healthcare provider clean the medical instrument between each use or between each patient. This can mean that a particular medical instrument may cleaned thousands of times within the course of a year. It is even possible that a medical instrument may be cleaned tens of thousands of times within its service life.

A typical cleaning and disinfection protocol may require a number of steps. For example the healthcare provider may first clean the medical instrument to remove visible contaminates from its exterior surface. Next the medical instrument may be disinfected using a disinfecting liquid or a textile impregnated with the disinfecting liquid. After this the medical instrument is allowed to dry.

A challenge in cleaning such medical instruments is that fluids used for the cleaning and/or disinfecting steps can destroy electronic components or delicate instruments used for performing the diagnostic tests if such fluids enter into the interior volume of the medical instrument, e.g. via the test element port. Ports used to insert biological samples or test elements or test strips not only need to be sealed against these fluids, but they also need to be able to be reliably sealed for tens of thousands of cycles.

United States patent application US 2012/0150448 A1 discloses a hand held analyte measurement system with a test strip port.

U.S. Pat. No. 8,158,081 B2 discloses an analyte monitoring device with a cover for covering an opening in the analyte meter. The cover is on the exterior of the analyte meter.

The document. ACCU-CHEK Inform II BLOOD GLUCOSE MONITORING SYSTEM Operator's Manual, version 3.0. (Roche Diagnostics GmbH, Mannheim, Germany, March 2013; available online at http://www.accu-chekinformii.com/pdf/05234646002_ACl2_OpsMan.pdf) describes a cleaning method for a handheld blood glucose monitoring system on page 124 to 131.

European Patent application publication EP 2741076 A1 pertains to a biological sample measurement device, which is intended to be easier to use. To achieve this object, the present invention comprises a main body case having a sensor insertion opening into which a sensor for measuring biological samples is inserted, a connection terminal provided within the main body case behind the sensor insertion opening, and a shutter that is provided within the main body case between the sensor insertion opening and the connection terminal and that opens and closes the sensor insertion opening.

PCT patent application publication WO 2010/024971 A1 discloses a device for preventing electrical shock from a device with electrical interfaces. A shutter or other barrier associated with the device that physically prevents access or contact to one of the electrical interfaces while another electrical interface is in use.

United States Patent application publication US 2010/0249567 (hereafter "the '567 application") discloses a portable blood sugar measuring device comprising a tape unit for winding a test tape forward in sections, a detection unit for detecting measured values on the sections of tape to which body fluid has been applied, and a housing to hold the tape unit and detection unit. The tape unit and/or the detection unit can be deflected relative to the housing from an operating position against a flexible restoring element when subjected to a shock load. Also disclosed is a novel cover having open and closed positions. The cover is positioned at an opening of the housing through which the receiving site of the tape unit protrudes. The cover thus protects the receiving site from external effects when the cover is in the closed position. Similarly, the receiving site is accessible to apply body fluid thereto when the cover is in the open position.

SUMMARY

The invention provides for a method of operating a medical instrument and a medical instrument in the independent claims. Embodiments are given in the dependent claims.

As will be appreciated by one skilled in the art, aspects of the present invention may be embodied as an apparatus, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer executable code embodied thereon.

Any combination of one or more computer readable medium(s) may be utilized. The computer readable medium may be a computer readable signal medium or a computer readable storage medium. A 'computer-readable storage medium' as used herein encompasses any tangible storage medium which may store instructions which are executable by a processor of a computing device. The computer-readable storage medium may be referred to as a computer-readable non-transitory storage medium. The computer-readable storage medium may also be referred to as a tangible computer readable medium. In some embodiments, a computer-readable storage medium may also be able to store data which is able to be accessed by the processor of the computing device. Examples of computer-readable storage media include, but are not limited to: a floppy disk, a magnetic hard disk drive, a solid state hard disk, flash memory, a USB thumb drive, Random Access Memory (RAM), Read Only Memory (ROM), an optical disk, a magneto-optical disk, and the register file of the processor. Examples of optical disks include Compact Disks (CD) and Digital Versatile Disks (DVD), for example CD-ROM, CD-RW, CD-R, DVD-ROM, DVD-RW, or DVD-R disks. The term computer readable-storage medium also refers to various types of recording media capable of being accessed by the computer device via a network or communication link. For example a data may be retrieved over a modem, over the internet, or over a local area network. Computer executable code embodied on a computer readable medium may be transmitted using any appropriate medium, including but not limited to wireless, wire line, optical fiber cable, RF, etc., or any suitable combination of the foregoing.

A computer readable signal medium may include a propagated data signal with computer executable code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

'Computer memory' or 'memory' is an example of a computer-readable storage medium. Computer memory is any memory which is directly accessible to a processor. 'Computer storage' or 'storage' is a further example of a computer-readable storage medium. Computer storage is any non-volatile computer-readable storage medium. In some embodiments computer storage may also be computer memory or vice versa.

A 'processor' as used herein encompasses an electronic component which is able to execute a program or machine executable instruction or computer executable code. References to the computing device comprising "a processor" should be interpreted as possibly containing more than one processor or processing core. The processor may for instance be a multi-core processor. A processor may also refer to a collection of processors within a single computer system or distributed amongst multiple computer systems. The term computing device should also be interpreted to possibly refer to a collection or network of computing devices each comprising a processor or processors. The computer executable code may be executed by multiple processors that may be within the same computing device or which may even be distributed across multiple computing devices.

Computer executable code may comprise machine executable instructions or a program which causes a processor to perform an aspect of the present invention. Computer executable code for carrying out operations for aspects of the present invention may be written in any combination of one or more programming languages, including an object oriented programming language such as Java, Smalltalk, C++ or the like and conventional procedural programming languages, such as the "C" programming language or similar programming languages and compiled into machine executable instructions. In some instances the computer executable code may be in the form of a high level language or in a pre-compiled form and be used in conjunction with an interpreter which generates the machine executable instructions on the fly.

The computer executable code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described with reference to flowchart illustrations and/or block diagrams of methods, apparatus (systems) and computer program products according to embodiments of the invention. It will be understood that each block or a portion of the blocks of the flowchart, illustrations, and/or block diagrams, can be implemented by computer program instructions in form of computer executable code when applicable. It is further under stood that, when not mutually exclusive, combinations of blocks in different flowcharts, illustrations, and/or block diagrams may be combined. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The invention provides for a method of operating the medical instrument and a medical instrument in the independent claims. Embodiments are given in the dependent claims.

In one aspect the invention provides for a method of operating a medical instrument. The medical instrument is an analyzer for performing a measurement on a biological sample using a test strip. The analyzer could for example be a handheld analyzer or a table top analyzer.

A biological sample as used herein encompasses also any chemical product derived, copied, replicated, or reproduced from a sample taken from an organism.

A test strip as used herein encompasses a ribbon-shaped substrate for receiving a liquid biological sample. A test strip is a disposable element containing chemicals that react with the analyte to be determined in the biological sample and is used for a single measurement. The determination of the analyte can be performed using different technologies, e.g. optical or electrochemical methods, and therefore the test strip comprises specific measurement structures to perform these measurements, e.g. optical test fields or electrode structures.

The medical instrument comprises a housing with an exterior surface. The housing comprises an interior surface surrounding an interior volume. In other words an analytical unit is inside of the housing of the medical instrument.

The medical instrument further comprises an analytical unit for analyzing the test strip. The analytical unit is within the interior volume. The analytical unit comprises a test strip mount configured for receiving the test strip to perform the measurement. The medical instrument further comprises a test strip port between the exterior surface and the interior surface. The test strip port is configured for receiving the test strip. The test strip port is aligned with the test strip mount along an insertion direction. The medical instrument further comprises a shutter for sealing the test port. The shutter is configured for being in an open position and a closed position. The shutter is within the interior volume. The shutter is configured for sealing the test port when in the closed position. The shutter comprises a test strip opening. The test strip opening is aligned with the test strip port and the test strip mount when the shutter is in the open position.

The shutter has a first sealing surface. The test strip port has a second sealing surface. The first sealing surface and the second sealing surface are configured to mate in the closed position. The shutter comprises a mechanism for moving the shutter between the open position and the closed position. Moving the shutter between the closed position and the open position comprises a rotation of the shutter parallel to the insertion direction. In other words the shutter is operable for being rotated between the closed and the open position.

The medical instrument further comprises an actuator for actuating the mechanism to move the shutter between the open position and the closed position. The actuator for instance may be a motor or other device which may be controlled by a processor for controlling the medical instrument for opening and closing the shutter. In other embodiments there may be a mechanism which is actuated by hand. For example a lever or other device might be used for actuating the mechanism.

The method comprises the step of controlling the actuator to actuate the mechanism to move the shutter into the open position. The method starts by the shutter being in the open position. Next a biological sample is placed onto a test strip. The next step in the method is to insert the test strip into the test strip port such that the test strip passes through the test strip support and into the test strip mount. The steps of placing the sample onto the test strip and inserting the test strip into the test strip port can also be performed in reverse order, in particular if the test strip comprises sample transport structures (e.g. a capillary channel) which can transport the biological sample from a sample application port of the test strip which is located outside of the medical instrument if the test strip is inserted into the test strip port to the measurement structures of the test strip which are located inside of the medical instrument if the test strip is inserted into the test strip port. The test strip is now in a position where the measurement of the biological sample can be performed by the analytical unit. The method further comprises analyzing the test strip with the analytical unit to perform the measurement.

Next the method comprises removing the test strip from the medical instrument. The next step in the method is to control the actuator to actuate the mechanism to move the shutter into the closed position. The test strip port is now sealed by mating the first sealing surface and the second sealing surface. The method further comprises cleaning the exterior surface of the medical instrument. Cleaning may include cleaning and/or disinfecting.

This embodiment may have the benefit of providing for a medical instrument which can be more readily cleaned. This for instance may be beneficial for test strip analyzers that are used in a clinical situation in a doctor's office or a hospital. In such situations the medical instrument should be cleaned after every use to ensure proper hygiene and reduce the chances that an infection is spread. Having the shutter within the interior volume makes it easier to clean the medical instrument.

In clinical use, healthcare professionals are typically required to follow a cleaning protocol when using a medical instrument more than once. An typical cleaning protocol usually requires the health care professional to clean the outer surface of the medical instrument to ensure that there is no organic material or other containments visible. After this step the medical professional will usually clean the surface with a liquid disinfectant to further clean the surface and kill or deactivate any microorganism such as bacteria or viruses. The liquid disinfectant could for example be provided in the form of a wipe or towel that is infused or saturated with the liquid disinfectant. After this cleaning, the health care professional allows the surface to dry and/or wipes it clean. Medical instruments used in clinics or hospitals may be used repeatedly during the day and are cleaned according to such a protocol after each use. This may result the medical instrument being cleaned thousands of times during the lifetime of its usage. The method and medical instrument may provide for a medical instrument that may be more easily cleaned and/or able to better survive repeated cleanings and/or sterilizations.

In the '567 application, there are two shutters 48 which are half-shell shaped and which rotate about the pivot 50. In par. [0039] it is disclosed that the shutters are able to screen the receiving site 44 from contamination. However, in FIG. 3 of D3 it is clear that the shutters are circular. It is not disclosed if these shutters are sealed or not where the shutters 48 contacts the housing 10. It is likely that the shutters 48 would not be able to form a reliable seal with the housing to prevent fluid from entering the device of D3 during the performance of repeated cleaning protocols.

In the '567 application, the shutters 48 close the opening 42 with two half-shell flaps. If the shutters of the device of the '567 application are closed, such as is illustrated in FIG. 5, the outer surface of the shutters 48 will be exposed when the device is cleaned. The point where the two shutters touch to close off the opening 42 is not within an interior volume of the device.

In contrast, in the present embodiment the shutter is within the interior volume. This may have the benefit of reducing the area of the shutter exposed during cleaning of the medical instrument.

In the '567 application there are two shutters 48 that are rotated into position. In contrast in the present embodiment there is only one shutter. The present embodiment may have the advantage that there are fewer moving parts.

In the '567 application the two shutters 48 are rotated perpendicular to the direction in which the receiving head 40 extends through the opening 10. The mechanism of the '567 application would be unsuitable for a test strip. The mechanism in the '567 application is for closing off a large receiving head and is not suitable for closing an opening for a test strip.

In another embodiment, the second sealing surface is within the interior volume.

In another embodiment, the second sealing surface is on the on the interior surface.

In another embodiment, in the open position the first sealing surface is within the interior volume.

In another embodiment, the first sealing surface and the second sealing surface form the seal within the interior volume when the shutter is in the closed position. This may have the advantage of minimizing the surface area of the In another embodiment, the test strip port is an opening in the housing.

In another embodiment, the test strip port contacts the interior surface and the exterior surface.

In another embodiment, the test strip opening is a hole within the shutter. Having the test strip opening as a hole within the shutter may have the advantage that the test strip opening is kept clean when the shutter is closed and when the medical instrument is cleaned cleaning agent would not be able to come into contact with the test strip opening.

In another embodiment, the test strip opening is a test strip support.

In another aspect the invention provides for a medical instrument. The medical instrument is an analyzer for performing a measurement on a biological sample using a test strip. The medical instrument comprises a housing with an exterior surface. The housing comprises an interior surface surrounding the interior volume. The medical instrument further comprises an analytical unit for analyzing the test strip. The analytical unit is within the interior volume. The analytical unit comprises a test strip mount configured for receiving the test strip to perform the measurement. The medical instrument further comprises a test strip port between the exterior surface and the interior surface.

The test strip port is configured for receiving the test strip. The test strip port is aligned with the test strip mount along an insertion direction. The medical instrument further comprises a shutter for sealing the test port. The shutter is configured for being in an open position and a closed position. The shutter is within the interior volume. The shutter is configured for sealing the test port when in the closed position. The shutter comprises a test strip opening. The test strip opening is aligned with the test strip port and the test strip mount when the shutter is in the open position. The shutter has a first sealing surface.

The test strip port has a second sealing surface. The first sealing surface and the second sealing surface are configured to mate in the closed position. By mating, that means that the first sealing surface and the second sealing surface seal the test strip port. The shutter comprises a mechanism for moving the shutter between the open position and the closed position. Moving the shutter between the closed position and the open position comprises a rotation of the shutter parallel to the insertion direction. The medical instrument further comprises an actuator for actuating the mechanism to move the shutter between the open position and the closed position.

In some examples the test strip opening may be a hole or opening in the shutter. In other examples the test strip opening may be a region that is cut away from the shutter. So in some examples the test strip opening is a hole in the shutter. In other examples the test strip opening may be formed by an edge of the shutter.

In another embodiment the medical instrument is battery powered. The actuator for instance may be powered by the battery. The analytical unit may also be powered by the battery.

In another embodiment the battery is a rechargeable battery.

In another embodiment the interior volume is hermetically sealed from the exterior surface when the shutter is in the closed position. This may have the benefit that when the shutter is in the closed position the medical instrument may be more readily cleaned.

In another embodiment, the interior volume is watertight when the shutter is in the closed position. It is understood that herein the term watertight herein may in some cases apply to either water only, to some liquids, or to liquids in general.

In another embodiment, the interior volume is watertight from the exterior surface when the shutter is in the closed position.

In another embodiment, when the shutter is in the closed position the shutter and test port fit together so tightly that liquid is unable to enter the interior volume through the test port.

It is understood herein that the term "sealed" as used herein means that when the shutter is in the closed position the shutter prevents the transport of gas and/or liquid through the test port.

In another embodiment the first and second sealing surfaces may have different properties. For example one could have a flexible surface such as a gasket and one could be a rigid or hard surface. In another example both surfaces may be similar, both may for example have a flexible or gasket-like surface.

In another embodiment the actuator is a manually operated lever, wheel, or crank.

In another embodiment the actuator may be a motor, stepper motor or other actuator, e.g. a stroke magnet.

In another embodiment the actuator comprises a motor. The medical instrument further comprises a memory for storing machine-executable instructions. The medical instrument further comprises a processor for controlling the medical instrument. Execution of the machine-executable instructions further causes the processor to control the motor to actuate the mechanism to move the shutter in the open position. Execution of the machine-executable instructions further cause the processor to analyze the test strip with the analytical unit to perform the measurement when the test strip is inserted into the test strip mount and the biological sample is placed on the test strip.

Execution of the machine-executable instructions further cause the processor to control the motor to actuate the mechanism to move the shutter in the closed position when the test strip is removed from the test strip mount and the test strip port. In some examples the medical instrument may automatically detect when the test strip is removed and controls the motor automatically. In other examples there may be a button or other user interface which the operator of the medical instrument uses to inform the processor that the test strip has been removed.

In another embodiment the shutter mechanism comprises a shutter shaft fixed to the shutter. The shutter shaft is configured for rotating about the rotational axis. The rotational axis is parallel to the insertion direction. The shutter is configured to rotate about the rotational axis in order to move between the open position and the closed position.

In another embodiment, the shutter mechanism comprises a shutter shaft that is configured for rotating about a rotational axis. Moving the shutter between the closed position and the open position comprises a rotation of the shutter about the rotational axis of the shutter shaft. The rotational axis is parallel to the insertion direction. The shutter is configured to rotate about the shutter shaft in order to move between the open position and the closed position.

In another embodiment the shutter shaft has a fixed position along the rotational axis. In this embodiment the actuator rotates the shutter shaft into position and the shutter shaft does not experience any linear translation along the rotational axis. This embodiment may have the benefit that it is a simple mechanism with a minimal number of moving parts.

In another embodiment the shutter shaft is configured both for rotational and translational motion along the rotational axis. The shutter further comprises an actuator shaft configured for rotational motion along a driving axis. The actuator shaft is rotationally connected to the actuator. The driving axis is parallel to the rotational axis. The shutter mechanism is configured such that the rotational motion of the driving axis causes rotational motion of the actuator shaft about the rotational axis. The shutter mechanism is further configured such that the rotational motion of the driving axis causes translational motion of the actuator shaft along the rotational axis.

This embodiment may have the benefit that the combined rotational and linear motion of the shutter enables for a shutter that may be opened and sealed a larger number of times. The shutter mechanism may be implemented in a variety of different ways. For example the shutter shaft and the actuator shaft may be connected by a gear mechanism. For example the shutter shaft and the actuator shaft could be connected by screw threads or other linear gear system that both rotates and moves the shutter shaft. In other examples a system of cams could be used to control the rotation and linear motion of the shutter shaft.

In the '567 application, as was described previously, the opening 42 is closed by two shell like shutters 48. It is not disclosed how or if they are sealed, but if they were it would be necessary to seal where the surfaces of the housing 10 contact the shutters 48. This would be a sliding contact that would wear any seal quickly and lead to failure. Additionally, the housing 10 and the shutters 48 would need to be manufactured to tight dimensional tolerances in order for the shutters to even seal. In contrast, the above mentioned embodiment may have the advantage that the seal will last a larger number of times and can seal the test strip port when manufactured to lower dimensional tolerances.

In another embodiment the driving axis is coaxial with the rotational axis. The shutter mechanism comprises a bearing sleeve for receiving the actuator shaft and the shutter shaft. The shutter mechanism comprises a guiding pin connected to the shutter shaft. The bearing sleeve is connected to the housing. That is say the bearing sleeve is rigidly or permanently connected to the housing. The bearing sleeve comprises a guideway for the guiding pin to control the rate of translational motion of the shutter shaft relative to the rotational motion of the shutter shaft. The guideway and the pin function essentially as a cam. As the actuator shaft is rotated this may cause the shutter shaft to rotate also and the pin is then forced to move in the guideway. The pin then controls the linear position of the shutter shaft as the shutter is rotated. This may be used to quickly rotate the shutter into position and then to force the shutter closed or open.

In another embodiment the actuator is a rotational motor.

In another embodiment the shutter shaft is configured for translational motion along the rotational axis. The shutter shaft further comprises an actuator shaft configured for translational motion along a driving axis. The actuator shaft is configured for translationally driving the shutter shaft along the rotational axis. The driving axis is parallel to the rotational axis. The shutter mechanism is configured such that the translational motion of the driving axis causes rotational motion of the actuator shaft about the rotational axis. The shutter mechanism is further configured such that translational motion of the driving axis causes translational motion of the actuator shaft along the rotational axis. In this embodiment the actuator shaft pushes the shutter shaft along the rotational axis. The mechanism is configured such that this translational motion causes not just the translational motion of the shutter shaft but also rotational motion. This mechanism could be implemented in a variety of ways. For example a spring or other elastic element could be used to return the shutter shaft to an original position for example in the open position or in the closed position. A keyway or cam or guideway could be used to control the rate of translational motion relative to the rotational motion.

In another embodiment the shutter mechanism further comprises an elastic element for returning or forcing the shutter into the open position or into the closed position.

In another embodiment the shutter mechanism further comprises a spring configured for returning or forcing the shutter into the open position or into the closed position.

In these embodiments the spring or elastic element could be configured to apply a translational force which returns the shutter to either the open or the closed position. When the actuator is no longer applying force, the spring or elastic element then moves the shutter back to its original position.

In an alternative, the spring or elastic element could be configured to apply a rotational force which is less than the rotational force applied by the actuator. The actuator could be configured such that it applies a force that overcomes the spring or elastic element and then moves the shutter into either the open or closed position. When the actuator is no longer applying force, the spring or elastic element then moves the shutter back to its original position.

In these embodiments the spring or elastic element could be strong enough so that, for example, the actuator is moved into the open position or into the closed position when the actuator is not in use. This may have several advantages. When the actuator is for example not powered the shutter could be forced open or closed.

The use of a spring or elastic element may also provide for more effective sealing when the spring or elastic element forces or returns the shutter into the closed position. If the first and/or second sealing surface are elastic their shape may permanently deform during the lifetime of the medical instrument. This may result in needing to close the shutter more to maintain an effective seal. Using a spring or elastic element may be beneficial because the spring or elastic element would force the shutter to seal. An alternative would be to adjust the position that the shutter is actuated to over a period of time. However this may be more complicated and/or require the attention of a service technician than using a spring or elastic element.

In another embodiment the driving axis is coaxial with the rotational axis. The shutter mechanism comprises a bearing sleeve for receiving the actuator shaft and the shutter shaft. The shutter mechanism comprises a guiding pin connected to the shutter shaft. The bearing sleeve is connected to the housing. The bearing sleeve comprises a guideway for guiding the pin to control the rate of rotational motion of the shutter shaft relative to translational motion of the shutter shaft.

In another embodiment the shutter mechanism comprises a spring or elastic element which restores the shutter to the open position or to the closed position.

In another embodiment the actuator is a linear actuator or a linear motor.

In another embodiment the medical instrument further comprises a user interface for receiving user input that indicates that the medical instrument has been cleaned. Execution of the machine-executable instructions further cause the processor to control the motor to actuate the mechanism to move the shutter in the open position after receiving the user input.

In another embodiment the medical instrument further comprises a detector for detecting if a test strip is inserted through the test strip port. Execution of the machine-executable instructions further causes the processor to control the motor to place the shutter in the closed position after the detector indicates that the test strip is not longer inserted through the test strip port. For example once a test strip is inserted into the test strip port whenever one is removed the shutter automatically closes. In some examples the detector for detecting if the test strip is inserted could be an optical detector. In other examples the detector may be a mechanical switch actuated if a test strip is inserted through the test strip port.

In another embodiment the first sealing surface is planar. The second sealing surface is also planar.

In another embodiment the first sealing surface is convex. The second sealing surface is concave.

In another embodiment the first sealing surface or the second sealing surface is formed by an elastic gasket.

In another embodiment the analytical unit is an optical test strip analyzer.

In another embodiment the analytical unit is an electrochemical test strip analyzer.

In another embodiment the analytical unit is a combination of an optical test strip analyzer and an electrochemical test strip analyzer.

It is understood that one or more of the aforementioned embodiments of the invention may be combined as long as the combined embodiments are not mutually exclusive.

BRIEF DESCRIPTION OF THE DRAWINGS

In the following embodiments of the invention are explained in greater detail, by way of example only, making reference to the drawings in which:

FIG. 13 illustrates a further example of a portion of a medical instrument;

FIG. 14 illustrates a further example of a portion of a medical instrument;

DETAILED DESCRIPTION

Figure 1:
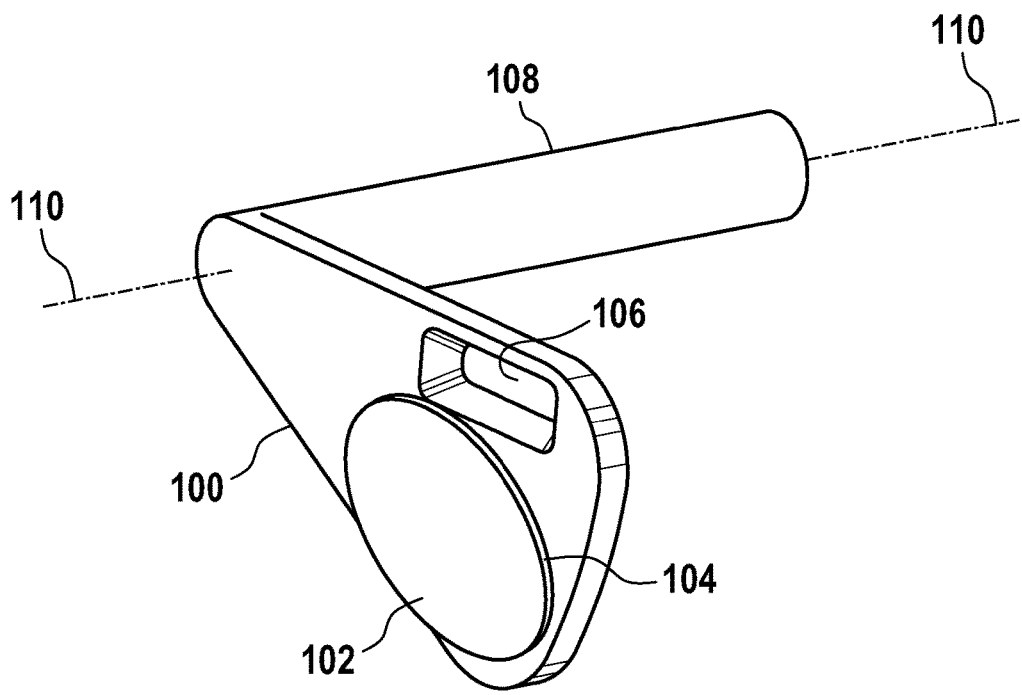
FIG. 1 shows a perspective view of a shutter.

Like numbered elements in these figures are either equivalent elements or perform the same function. Elements which have been discussed previously will not necessarily be discussed in later figures if the function is equivalent.

To measure the concentration of analytes in a body fluid, e.g. a glucose concentration from a small droplet of blood, disposable electrochemical capillary sensor test strips in combination with a meter to determine the concentration are used. For receiving the sensor strip there is a hole in the shell of the meter, commonly referred to as "strip-port" or a "test strip port."

In current medical instruments the strip-port is always open and there is no possibility to close it. U.S. Pat. No. 8,158,081 B2 describes a solution to close the strip-port.

Because the strip-port of current medical instruments is always open, the inner part of the meter is not prevented from contamination from outside. Fluids, dust and anything else can come through the hole of the strip-port to the interior of the meter. This can cause a technical fault, up to uselessness of the meter.

In the professional use case it is e.g. required, that the complete meter get cleaned and disinfected after every test or every patient. Therefore also the strip-port has to be cleaned and disinfected. It is likely that a small amount of cleaning or disinfection agents came through the hole of the strip-port into the interior of the meter. Some of these agents are very aggressive and the risk that the meter gets damaged is high.

Examples may have the feature of closing the strip-port every time it is not used. This means, that the strip-port only is open when a strip is inserted in the meter. When the measurement is ready and the strip is removed, the strip-port directly gets closed. The fastener or shutter is designed in the shape that the interior of the meter is prevented of contamination. Even when the strip-port get cleaned and disinfected, e.g. by whipping above the surface of the strip-port (e.g. with Clorox-wipes), there is no risk of contamination and the meter is prevented from technical faults and damages.

It is beneficial to make sure that the meter can be cleaned and disinfected very well. Therefore the surface of the meter and specially the area of the strip-port have to be as smooth as possible. To ensure that, the complete mechanical system is an inner part of the meter and on the surface of the meter there are no notches or chamfers.

The fastener (shutter mechanism) has a planar part (a shutter) and one cylindrical part (a shutter shaft) orthogonally to the planar area on the back side. The cylindrical part may be assembled in a bearing sleeve (or connector), in the way that it can rotate. The front side of the planar part may be a first sealing surface with a gasket (or elastic gasket). In the planar area (shutter) of the fastener there may be a hole as an opening for the sensor strip (test strip opening). The housing of the meter contains also a hole for the strip.

When the strip-port is closed, the hole of the planar area of the fastener is located inside of the meter (interior volume) and the gasket has contact with the housing. The housing, gasket, and planar part form a seal. Therefore, the inner part is protected from contamination.

To open the strip-port, the fastener rotates around its cylindrical part in the way that the hole is located in front of the opening of the housing. Now it is possible to insert the strip.

Figure 2:
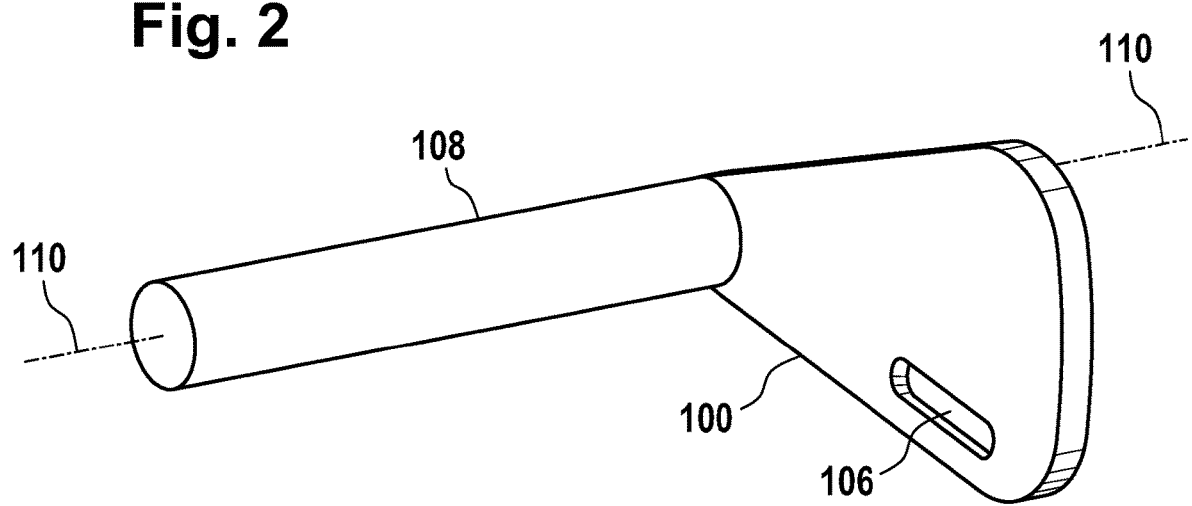
FIG. 2 shows an alternative perspective view of the shutter of FIG. 1.

FIGS. 1 and 2 show two different perspective views of the same shutter 100. The shutter can be seen as having a first sealing surface 102 that is formed by a gasket 104. There is a hole in the shutter 100 labeled 106 that is the test strip opening 106.

In this example the test strip opening is a hole through the shutter 100. However, the test strip opening 106 could also be formed by an edge of the shutter 100. That is to say the entire material in the vicinity of the test strip opening 106 could be removed instead. The shutter 100 is shown as being attached to a shutter shaft 108. The shutter shaft 108 has a rotational axis 110. The shutter mechanism shown in the following drawings illustrates how the shutter shaft 108 rotates about the axis 110 and causes the shutter 100 to move between the open and the closed position.

Figure 3:
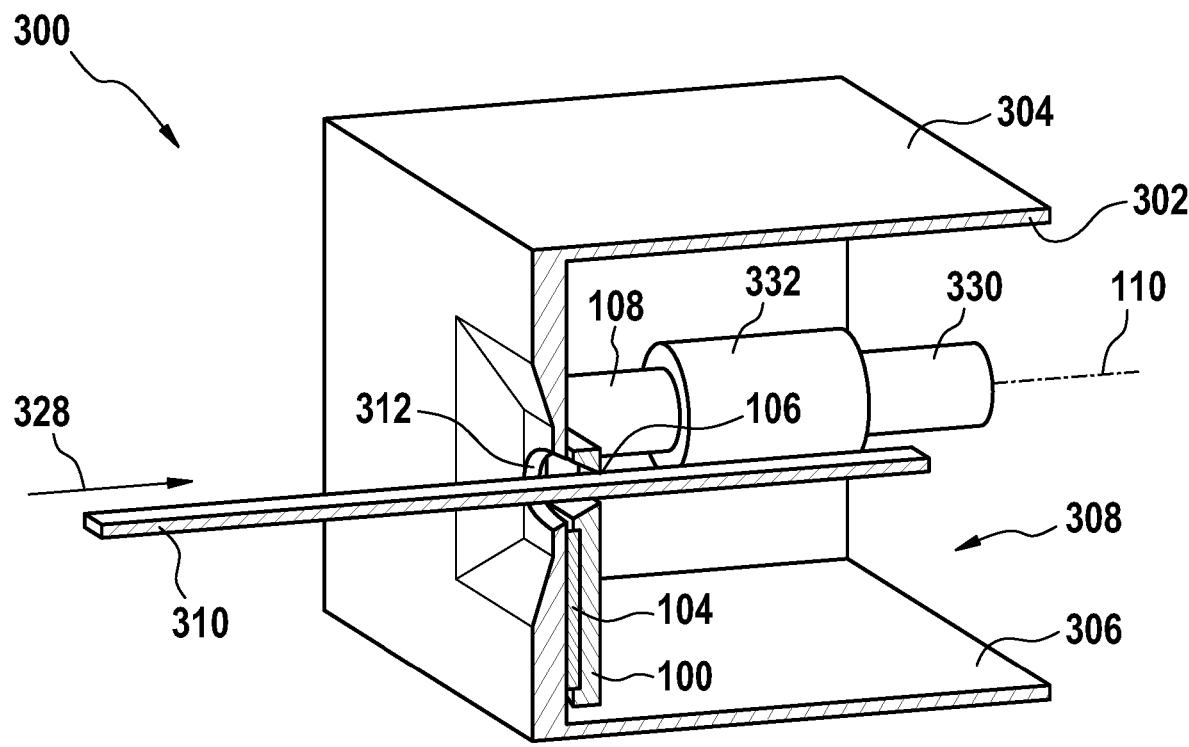
FIG. 3 illustrates an example of a portion of a medical instrument in a perspective view.
Figure 4:
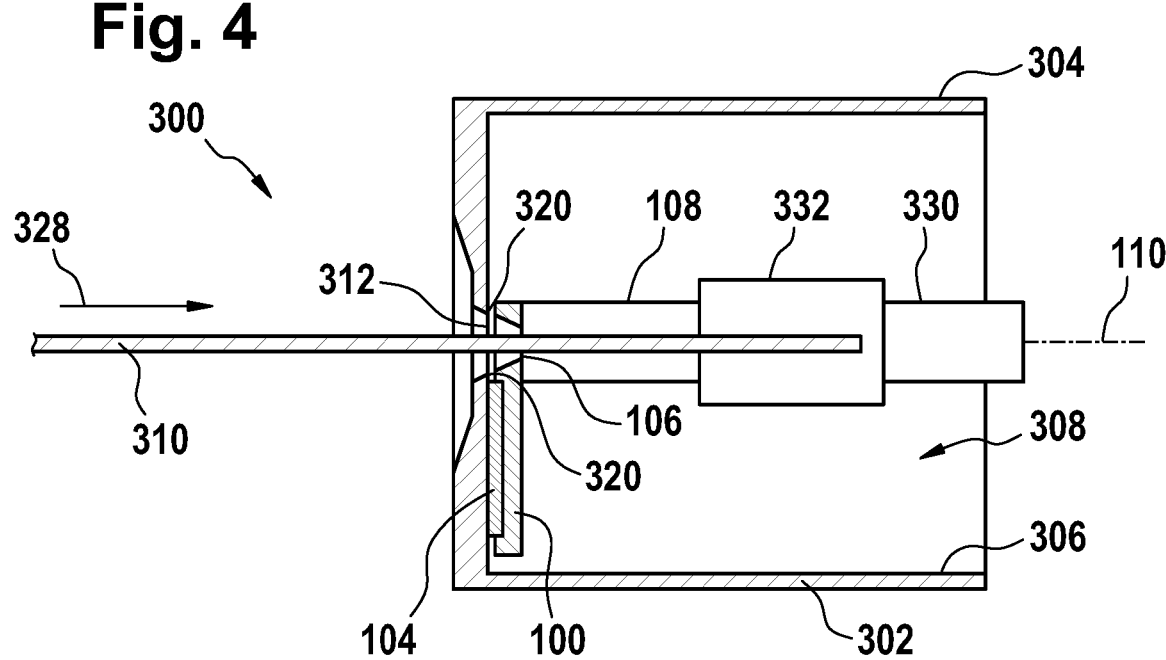
FIG. 4 shows the illustration of FIG. 3 from a side view.

FIG. 3 shows a perspective view of a portion of the medical instrument 300. FIG. 4 shows the side view of the same view that is shown in FIG. 3. The portion of the medical instrument 300 has a housing 302 that has an exterior surface 304 and an interior surface 306. The housing 302 surrounds an interior volume 308 that is bounded by the interior surface 306. Between the exterior surface 304 and the interior surface 306 there is a test strip port 312. A test strip 310 can be shown as being inserted along insertion direction 328 through the test strip port 312. In FIGS. 3 and 4 the shutter 100 is shown in the open position. The shutter shaft 108 is shown as being connected to an actuator shaft 330 via a coupling 332. In the examples shown in FIGS. 3 and 4 the distance of the shutter shaft along the rotational axis 110 is fixed.

Figure 5:
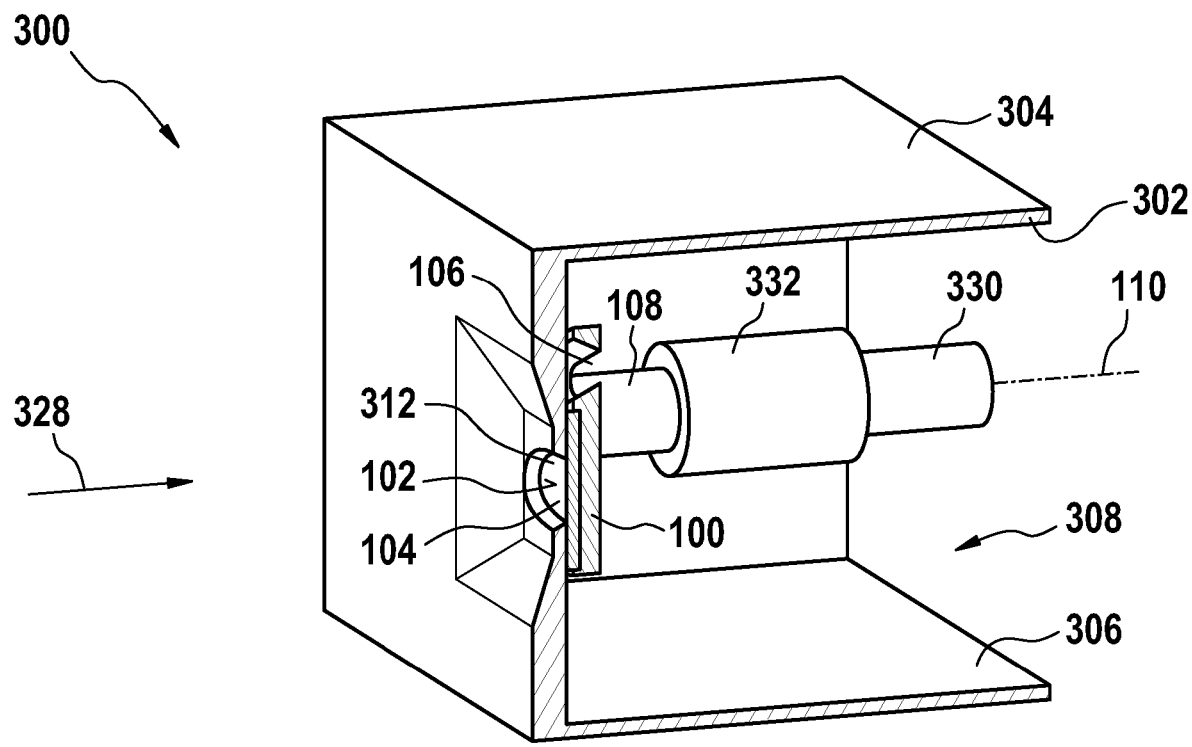
FIG. 5 shows a further perspective view of the portion of a medical instrument of FIG. 3.
Figure 6:
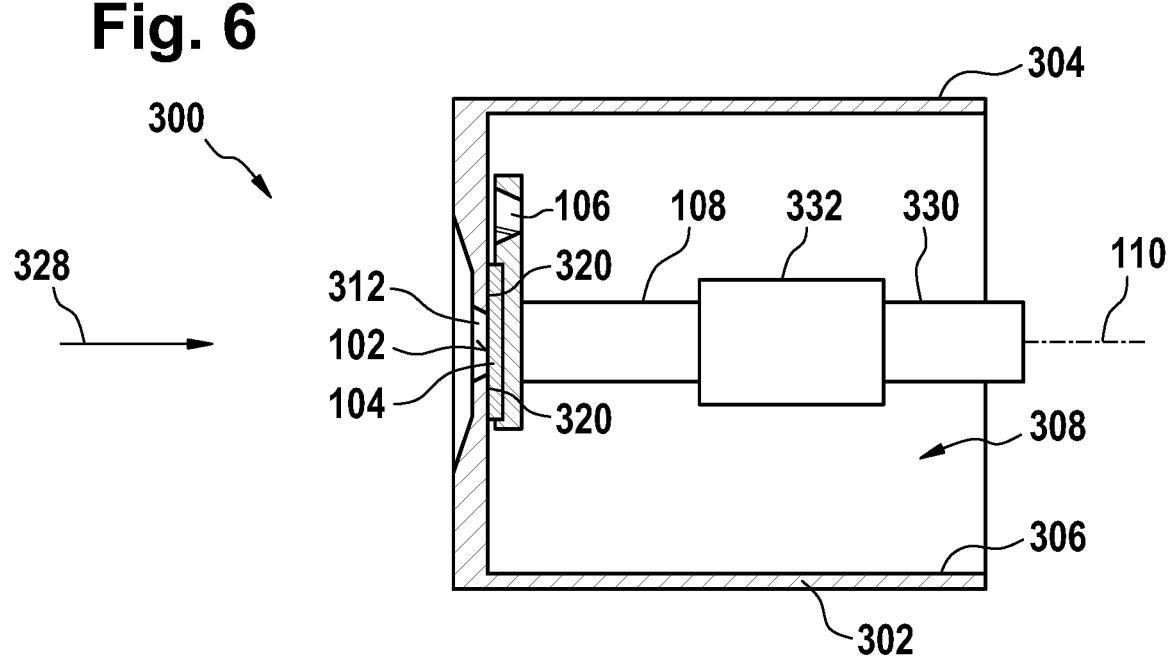
FIG. 6 shows the illustration of FIG. 5 from a side view.

FIGS. 5 and 6 show the same portion of the medical instrument 300 that was shown in FIGS. 3 and 4. In FIGS. 5 and 6 the shutter 100 is shown in the closed position. In the example shown in FIGS. 5 and 6 the actuator shaft 330 has been rotated. This caused the coupling 332 and the shutter shaft 108 to also rotate about the rotational axis 110. The test strip opening 106 has been rotated away from the test strip port 312 and instead the gasket 104 has been rotated into place such that the first sealing surface 102 comes in contact with the second sealing surface 320. The interior volume 308 is now sealed from the exterior surface 304. The medical instrument can for example now be cleaned with a liquid cleaning solvent or solution.

Another solution is that the movement of the cylindrical part is not only a rotational movement. The movement is divided into two sequences: A rotating and a linear sequence. The two sequences are realized with a link motion system or a linkage.

In the cylindrical part of the fastener is a hole for a pin. In the bearing sleeve there is guideway for the pin of the fastener.

The link motion is designed in the way, that there is a gap between gasket and housing in the opened position of the strip-port. When the strip-port is closed, the fastener (shutter) at first rotates (or primarily rotates with a smaller linear movement) and then makes the linear movement (or primarily a linear movement with a smaller rotational movement) with the linear movement the gap between housing and gasket get closed and the sealing is tight. By opening the strip-port the opposite occurs, at first the linear movement occurs and then the fastener rotates.

The advantage of this situation may be that there no friction (or at least reduced friction), because of the rotation, between the gasket and housing anymore.

Figure 7:
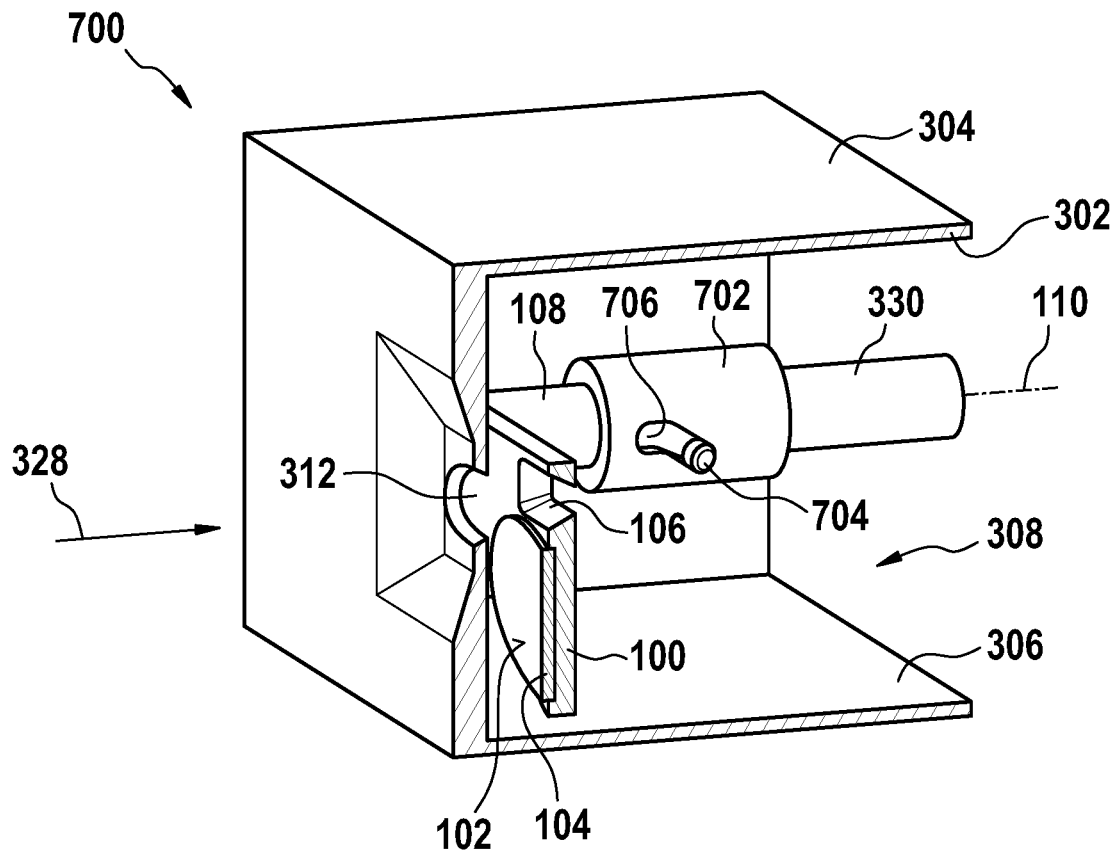
FIG. 7 illustrates a further example of a portion of a medical instrument in a perspective view.
Figure 8:
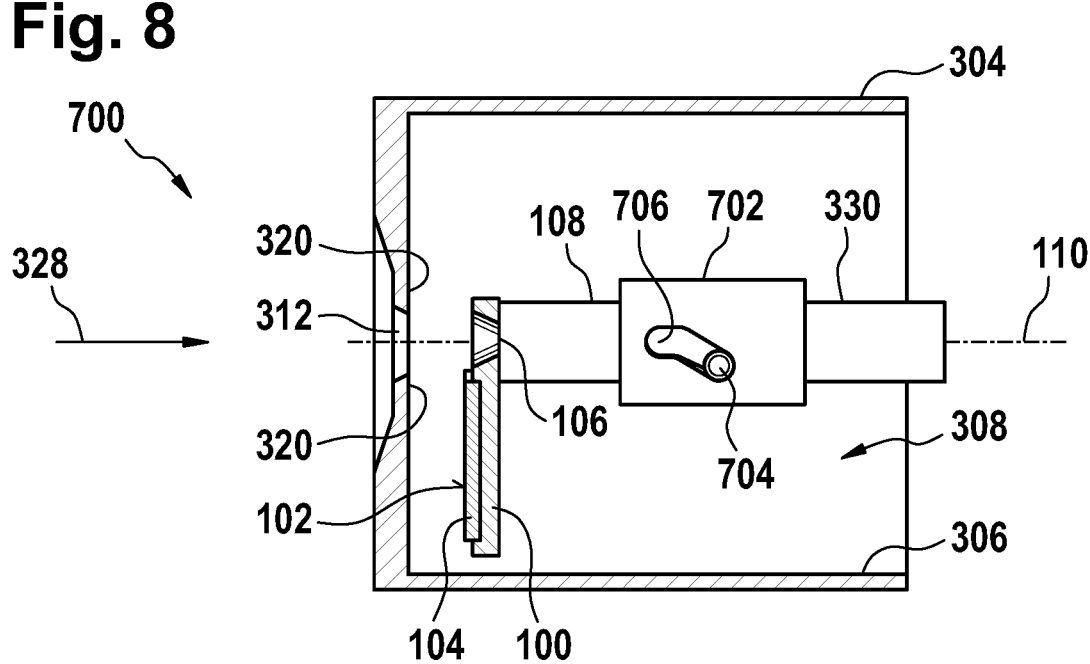
FIG. 8 shows the illustration FIG. 7 from a side view.
Figure 9:
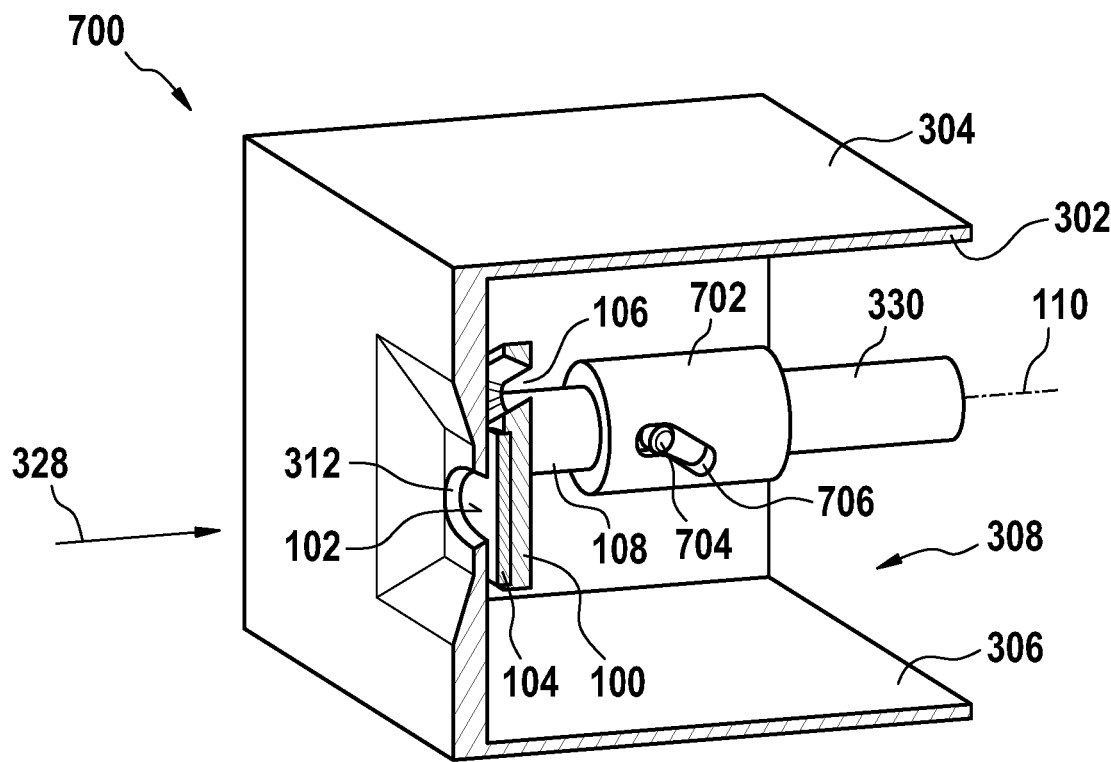
FIG. 9 shows a further perspective view of the portion of a medical instrument of FIG. 7.
Figure 10:
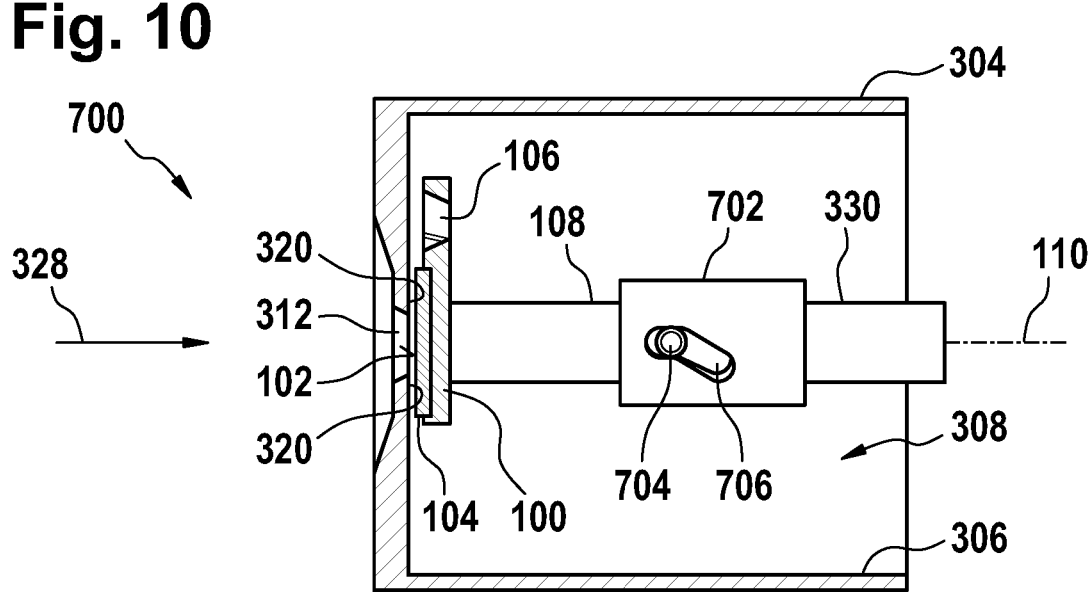
FIG. 10 shows the illustration of FIG. 9 from a side view.
Figure 11:
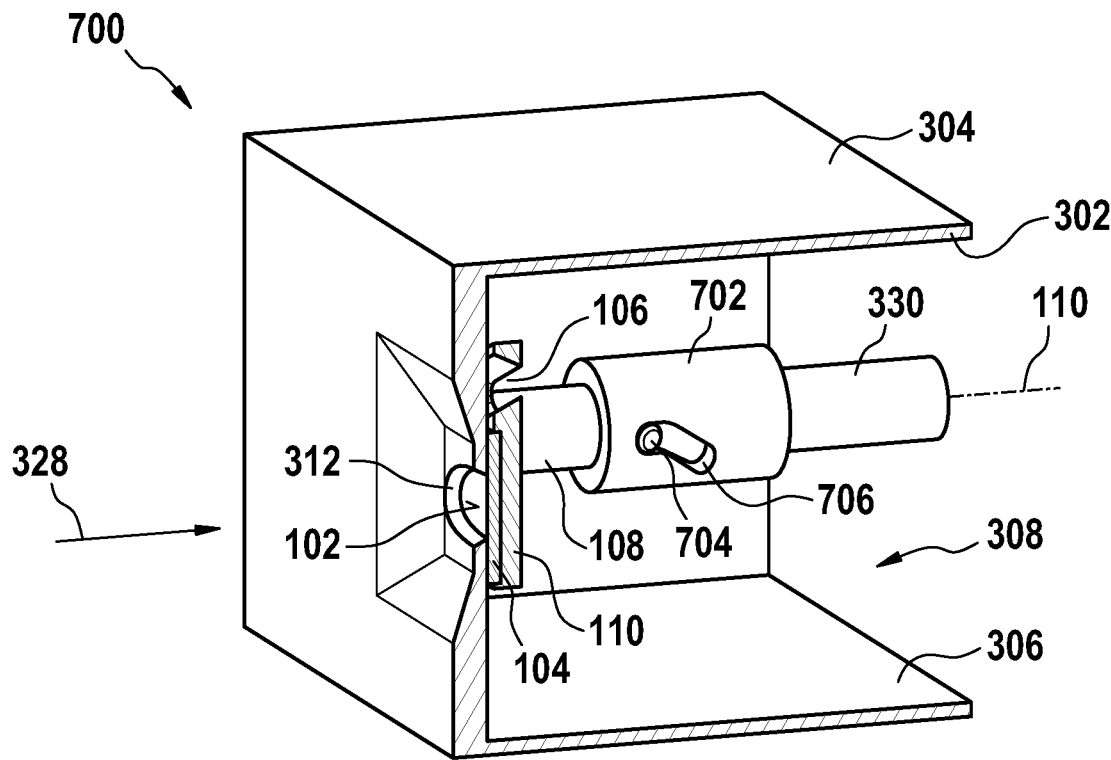
FIG. 11 shows a further perspective view of the portion of a medical instrument of FIG. 7.
Figure 12:
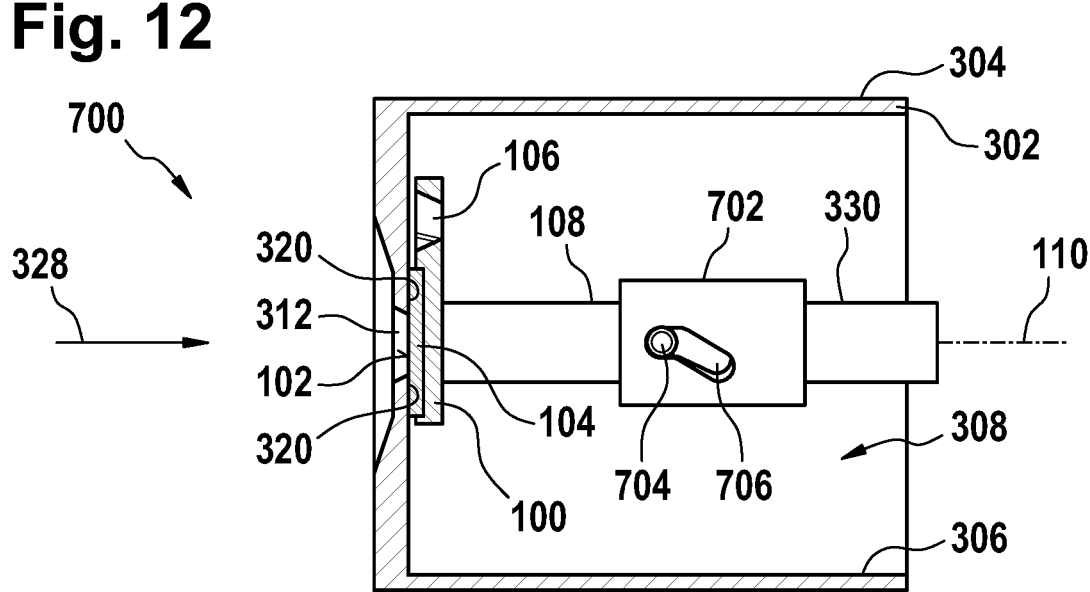
FIG. 12 shows the illustration of FIG. 11 from a side view.

FIGS. 7, 8, 9, 10, 11 and 12 illustrate a further example of a portion of a medical instrument 700. FIGS. 7 and 8 show the shutter 100 in the open position. FIG. 7 is a perspective view and FIG. 8 is a side view of the perspective shown in FIG. 7. FIG. 9 shows the shutter 100 in an intermediate position between being open and closed. FIG. 9 is a perspective view and FIG. 10 is a side view of the perspective shown in FIG. 9. FIGS. 11 and 12 show the shutter 100 in the closed position. FIG. 11 shows a perspective view. FIG. 12 shows the side view of the perspective shown in FIG. 11.

In FIGS. 7 and 8 the test strip opening 106 is shown as being aligned with the test strip port 312 such that a test strip can be inserted along the insertion direction 328. The mechanism in FIGS. 7-12 is similar to that shown in FIGS. 1-4 except the coupling 332 has been replaced with a bearing sleeve 702. The bearing sleeve 702 is rigidly connected to the housing 302. During the actuation of the mechanism the bearing sleeve 702 does not move. There is a guiding pin 704 which is connected rigidly to the shutter shaft 108. The bearing sleeve 702 has a guideway 706 which receives the guiding pin 704. The actuator shaft 330 is connected to the shutter shaft 108 so that when the actuator shaft 330 make a translational movement along the rotational axis 110 the shutter shaft 108 rotates. The guideway 706 defines the rotational position of the shutter shaft 108 relative to the translational position of the shutter shaft 108.

For example, a rod or other driveshaft could be connected to a hole or cross-section in both the shutter shaft 108 and the actuator shaft 330 such that the shutter shaft 108 turns with the actuator shaft 330 but is free to move along the rotational axis 110. The combination of the guiding pin 704 and the guideway 706 controls the position of the shutter 100 along the rotational axis 110 as a function of the translational position of the shutter 110. This may be useful because the motion of the shutter as it is rotated into place along the rotational axis 110 can be controlled. For example in the example shown in FIGS. 1-4 the gasket 104 is always in contact with the interior surface 306. In the example shown in FIGS. 7-12 the gasket in the open position 104 does not contact the interior surface 306. This for example may result in reduced wear and tear on the gasket 104.

In FIGS. 9 and 10 it can be seen that the actuator shaft 330 has been moved along the rotational axis. This has also caused the shutter shaft 108 to rotate. The test strip opening 106 has been rotated away from the test strip port 312. The gasket 104 is now in position for sealing the test strip port 312. However, at this point it can be seen that the first sealing surface 102 is not yet in contact with the second sealing surface 320. The guideway 706 can be seen as sloping sharply towards the direction of the rotational axis 110. This shows that as the actuator shaft 330 is further moved forward the motion of the shutter 100 will be predominantly in a direction of the axis 110 causing the first 102 and second 320 sealing surfaces to contact thereby sealing the test strip port 312.

FIGS. 11 and 12 show the shutter after it has been moved into the closed position. It can be seen that the first 102 and second 320 sealing surfaces are now in contact and that the test strip port 312 is now sealed.

Figure 12A:
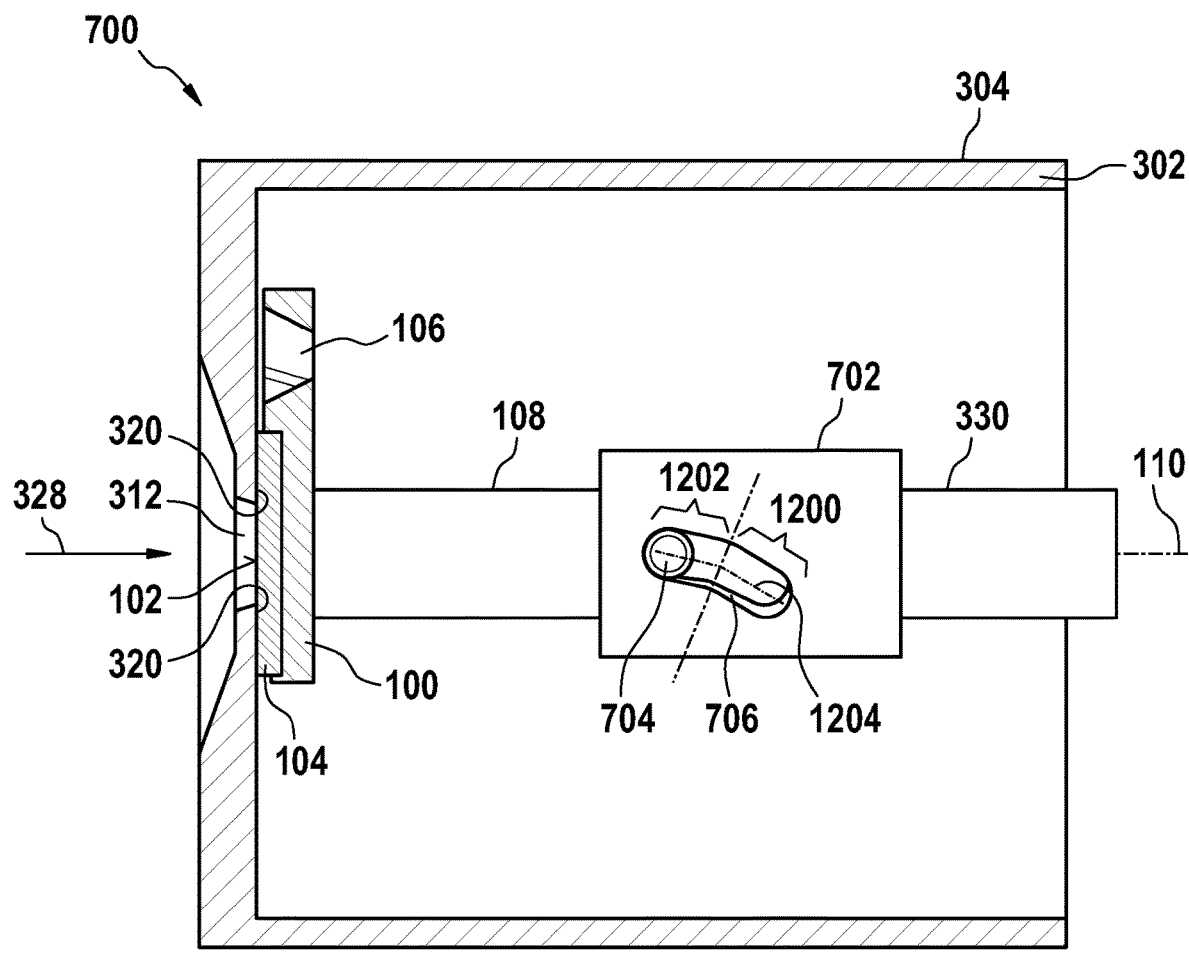
FIG. 12A shows an alternative to the example shown in FIG. 12.

FIG. 12A shows an alternative design for the guideway (706) of FIG. 12. In the example of 12A a rotational movement is used instead of a translational motion to actuate the shutter. A rotation of the shutter shaft 330 causes a translational movement (combined with a short rotation) of the shutter. In such an example the guideway may have a first section 1200 and a second section 1202 whereby the second section 1202 is closer to the first sealing surface 102 of the shutter than the first section 1200. Both the first 1200 and second section 1202, the guideway 706 is offset from the rotational axis 110. The guideway defines a path 1204 that the guiding pin 704 follows. When the path is projected onto the rotational axis 110, the angle of a small segment of the path 1204 relative to the rotational axis 110 is larger in the first section 1200 than in the second section 1202. This causes a more rotational movement if the pin is moved in the first section 1200 of the guideway and a more translational movement if the pin is move in the second section 1202 of the guideway.

In another example, the angle of the path 1204 relative to the rotational axis 110 in the first section 1200 is between 15° and 75°. In another examples the angle of the path 1204 relative to the rotational axis 110 in the first section 1200 is between 30° and 60°. In another examples the angle of the path 1204 relative to the rotational axis 110 in the first section 1200 is about 45°.

In another examples the angle of the path 1204 relative to the rotational axis 110 in the second section 1202 is between 0, 1° and 30°. In another example the angle of the path 1204 relative to the rotational axis 110 in the second section 1202 is between 0, 1° and 15°. In another example the angle of the path 1204 relative to the rotational axis 110 in the second section 1202 is between 0, 1° and 5°.

FIG. 13 shows a further example of a portion of a medical instrument 1300. In this example the actuator is a linear actuator 1302 or a lift magnet. This causes the actuator shaft 330 to exert a force and pull the shutter shaft 108 towards the linear actuator 1302. As the shutter shaft 108 is pulled a bearing sleeve 702 and a guiding pin, which is not shown in this Fig., cause the shutter 100 also to rotate and move into the open position. When the linear actuator 1302 ceases to exert a force on the actuator shaft 330 and the shutter shaft 108 then a spring 1306 or other elastic element force the shutter shaft 108 towards the interior surface 306 and the bearing sleeve 702 causes the shutter 100 to rotate and move back into the closed position. The example shown in FIG. 13 will automatically close when a force is no longer exerted by the linear actuator 1302. FIG. 13 shows an analytical unit 1304 which a test strip can be inserted into.

FIG. 14 shows a further example of a portion of a medical instrument 1400. The example shown in FIG. 14 is similar to that shown in FIG. 13 except in this example the actuator is a rotational actuator 1402 or a rotational motor. For example it could be stepper motor. The tip of the actuator shaft 330 in this example is threaded and mates with a threaded portion 1404 of the shutter shaft 108. As the actuator shaft 330 rotates the threads exert force on the shutter shaft 108 and the bearing sleeve 702 also causes the shutter 100 to rotate closed or open depending on whether the motor 1402 is going in one direction or the other.

Figure 15:
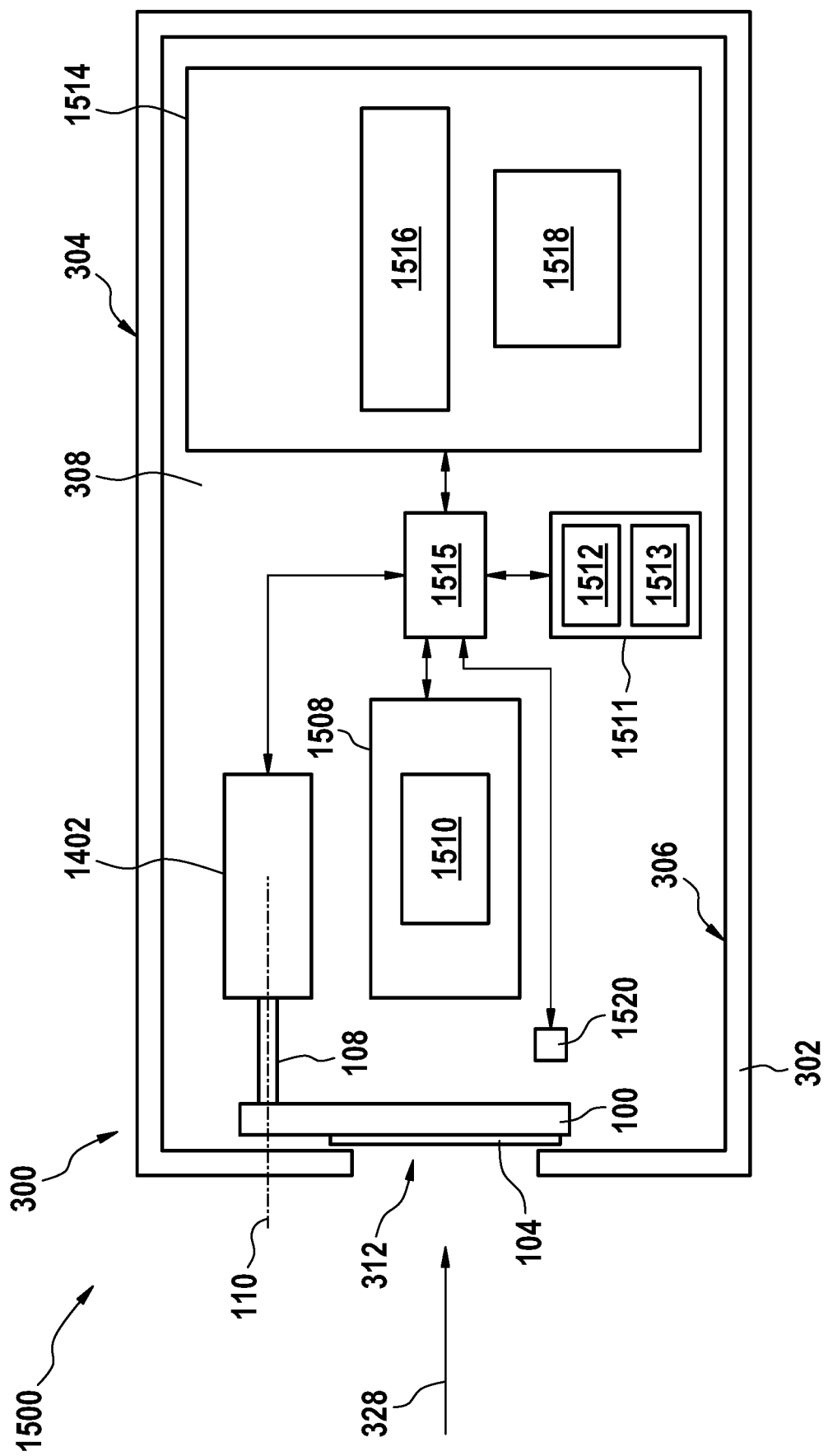
FIG. 15 illustrates an example of a medical instrument.

FIG. 15 shows an example of a medical instrument 1500 that incorporates the portion of the medical instrument 300 shown in FIGS. 1-14. The medical instrument has a housing 302 which has an exterior surface 304 and an interior surface 306. The interior surface 306 surrounds an interior volume 308. There is a test strip port 312 that is shown as being sealed by a shutter mechanism. The medical instrument could be altered to use the shutter mechanism according to any one of the mechanisms shown in FIGS. 1-14. Shown is a motor 1402 which has an actuator is used to drive shutter shaft 108. The motor 1402 can be used to automatically open or close the shutter 100. In this Fig. the shutter is shown as being closed and the test strip port 312 is sealed. When the test strip port 312 is open a test strip can be inserted into an analytical unit 1508. Inside the analytical unit 1508 there is a test strip mount 1510 which is configured for receive the test strip to perform a measurement.

Adjacent to the analytical unit 1508 and the shutter 100 is a strip detector 1520. The strip detector 1520 is a sensor (e.g. mechanical, optical, capacitive) which is used to detect the presence of a test strip within the medical instrument 1500. The medical instrument 1500 is further shown as containing a processor 1515. The processor 1515 is connected to the motor 1402, the analytical unit 1508, the optional strip detector 1520 and also a touch screen display 1514. The processor 1515 is further connected to a memory 1511. The processor 1515 is configured so that it can send and receive instructions for these components and control the operation and function of the medical instrument 1500. The memory 1511 is shown as containing a set of instructions 1512. Execution of the instructions 1512 enables the processor 1515 to control and operate the medical instrument 1500. The memory 1511 is further shown as containing at least one measurement 1513 that was acquired using the analytical unit 1508.

The touch screen 1514 is configured for displaying data and information as well as receiving input from an operator or user of the medical instrument 1500. For example when the medical instrument 1500 has its test strip port sealed as is shown in FIG. 15; it may display a message 1516 which asks if the cleaning protocol has been finished. The message could for example be "Finished with cleaning protocols?" There is a graphical user interface control element 1518 or button which the operator can use to inform the processor 1515 that a cleaning protocol has been finished. The control element 2518 could example have the text "Yes" displayed on it. For example when the cleaning protocol is finished, the processor 1515 may control the motor 1402 such that the shutter 100 is opened and it is then possible to insert a test strip into the analytical unit and mount it properly within the test strip mount 1510 so that a further measurement 1513 can be performed.

Figure 16:
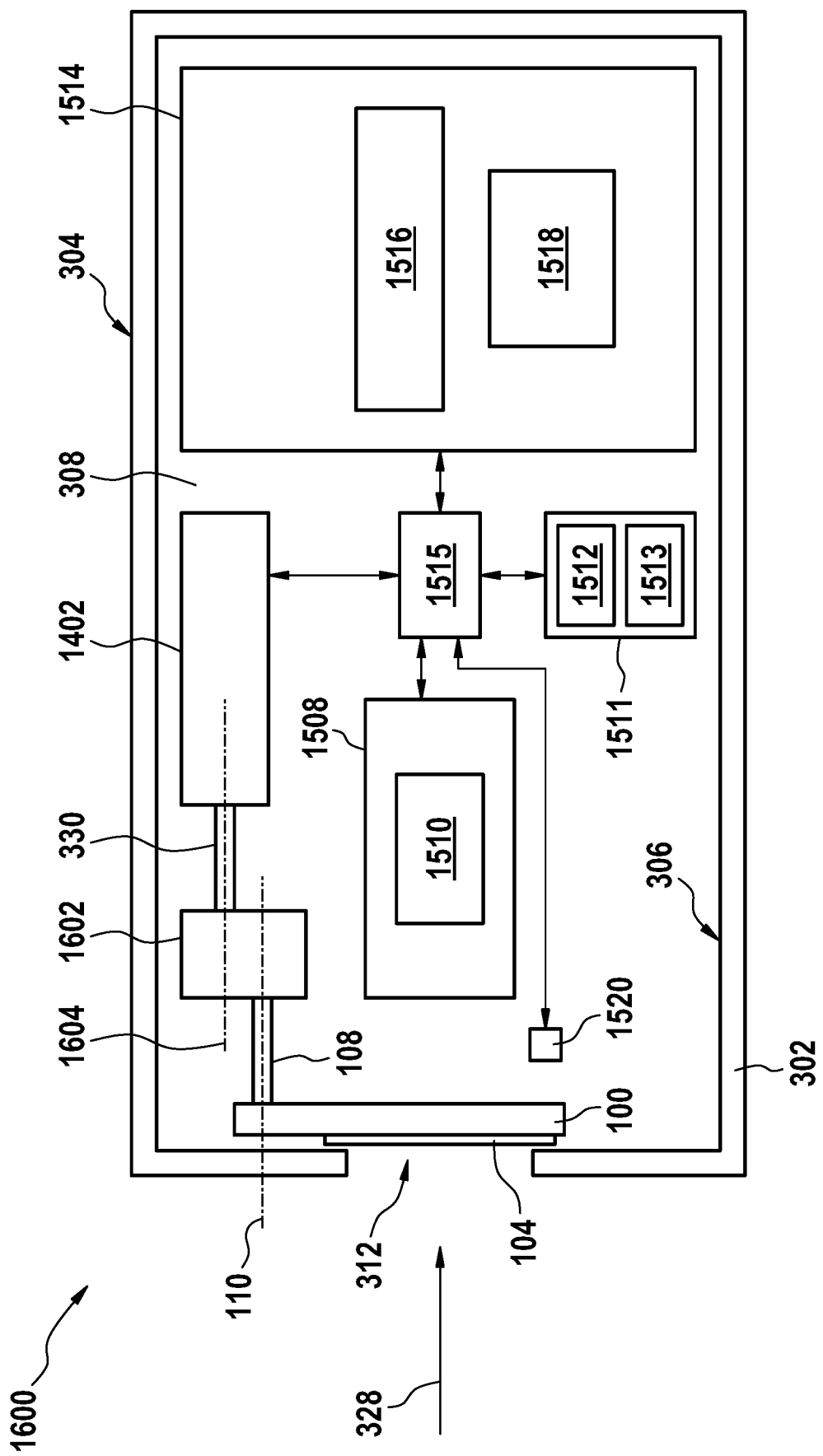
FIG. 16 illustrates a further example of a medical instrument.

FIG. 16 shows a further example of a medical instrument 1600. The medical instrument 1600 is similar to the medical instrument 1500 shown in FIG. 15. In this example there is a gearbox 1602 which is used to connect the shutter shaft 108 and the actuator shaft 1330. The stepper motor 1402 in this example is located off axis so that it has a separate driving axis 1604 that is parallel but is not coaxial with the rotational axis 110. The gearbox 1602 could be constructed in different ways. In one example it could simply rotate the shutter 100 as was shown in FIG. 15. In other examples the gearbox 1602 could also incorporate a translational motion so that the shutter 100 first moves into position and then closes.

Figure 17:
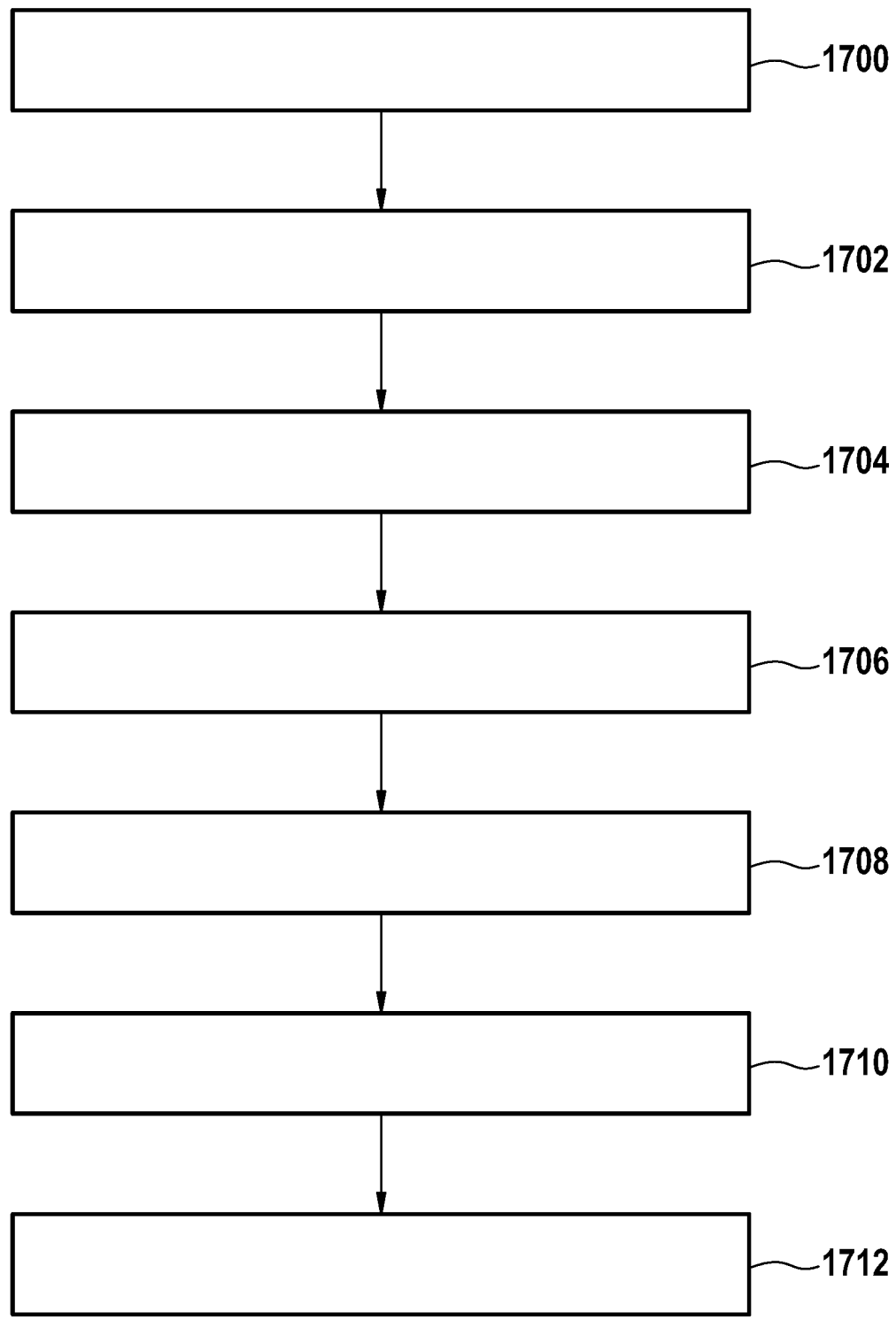
FIG. 17 shows a flow chart which illustrates an example of a method of operating the medical instrument of FIG. 15 or FIG. 16.

FIG. 17 shows a flowchart which shows one method of operating the medical instrument 1500 of FIG. 15 or the medical instrument 1600 of FIG. 16. First in step 1700 the actuator motor 1402 is controlled to move the shutter 100 into the open position. In FIGS. 15 and 16 the actuator 1402 is shown as being a motor 1402. In other examples the actuator for instance may be controlled or moved manually. Next in step 1702 a biological sample is placed onto a test strip.

Next in step 1704 a test strip is inserted into the test strip port 312 such that the test strip passes through the test strip support and into the test strip mount 1510. Next in step 1706 the test strip is analyzed with the analytical unit 1508 to perform the measurement 1513. Next in step 1708 the test strip is removed from the medical instrument 1500, 1600. Next in step 1710 the actuator 1402 is controlled to actuate the mechanism 1501 to move the shutter 100 into the closed position.

Finally in step 1712 the exterior surface 304 of the medical instrument 1500, 1600 is cleaned. The protocol for cleaning and disinfection the medical instrument 1500, 1600 may be performed with chemicals which easily damage the electronics and other components of the medical instrument 1500, 1600. For example in a clinical setting the medical instrument 1500, 1600 will likely be cleaned after every use or at least between use between different patients. The cleaning protocol may involve several steps. For example the protocol may begin with the medical instrument being wiped down to remove any obvious fluids or contaminants on the surface. Then, one or more steps where the medical instrument 1500, 1600 may be cleaned and/or disinfected with one or more chemical solutions may be performed. Finally, the medical instrument 1500, 1600 may be dried. Once the cleaning and disinfection protocol has been finished then the operator or user may elect to open the shutter 100 in preparation for inserting another test strip.

LIST OF REFERENCE NUMERALS

100 shutter
102 first sealing surface
104 gasket
106 test strip opening
108 shutter shaft
110 rotational axis
300 portion of medical instrument
302 housing
304 exterior surface
306 interior surface
308 interior volume
310 test strip
312 test strip port
320 second sealing surface
328 insertion direction
330 actuator shaft
332 coupling
700 portion of medical instrument
702 bearing sleeve
704 guiding pin
706 guideway
1200 first section
1202 second section
1204 path
1300 portion of medical instrument
1302 linear actuator or lift magnet
1304 analytical unit
1306 spring or elastic element
1400 portion of medical instrument
1402 rotational actuator
1404 threaded portion
1500 medical instrument
1502 mechanism portion
1504 motor
1506 actuator
1508 analytical unit
1510 test strip mount
1511 memory
1512 instructions
1513 measurement
1514 touch screen
1515 processor
1516 message "finished with cleaning protocols?"
1518 graphical user interface control element
1520 strip detector
1600 medical instrument
1602 gearbox
1604 driving axis
1700 control the actuator to actuate the mechanism to move the shutter in the open position
1702 place the biological sample on the test strip
1704 insert a test strip into the test strip port such that the test strip passes through the test strip support and into the test strip mount
1706 analyze the test strip with the analytical unit to perform the measurement
1708 remove the test strip from the medical instrument
1710 control the actuator to actuate the mechanism to move the shutter in the closed position; and
1712 clean the exterior surface of the medical instrument.

The invention claimed is:

1. A method of operating a medical instrument, wherein the medical instrument is an analyzer for performing a measurement on a biological sample using a test strip, wherein the medical instrument comprises:
   a housing with an exterior surface, wherein the housing comprises an interior surface surrounding an interior volume;
   an analytical unit for analyzing the test strip, wherein the analytical unit is within the interior volume, wherein the analytical unit comprises a test strip mount configured for receiving the test strip to perform the measurement;
   a test strip port between the exterior surface and the interior surface, wherein the test strip port is configured for receiving the test strip, wherein the test strip port is aligned with the test strip mount along an insertion direction;
   a shutter for sealing the test strip port, wherein the shutter is configured for being in an open position and a closed position, wherein the shutter is within the interior volume, wherein the shutter is configured for sealing the test strip port when in the closed position, wherein the shutter comprises a test strip opening, wherein the test strip opening is aligned with the test strip port and the test strip mount when the shutter is in the open position, wherein the shutter has a first sealing surface, wherein the test strip port has a second sealing surface, wherein the first sealing surface and the second sealing surface are configured to mate in the closed position, wherein the shutter comprises a shutter mechanism for moving the shutter between the open position and the closed position, wherein moving the shutter between the closed position and the open position comprises a rotation of the shutter parallel to the insertion direction, wherein the shutter mechanism comprises a shutter shaft fixed to the shutter, wherein the shutter shaft is configured for rotating about a rotational axis, wherein the rotational axis is parallel to the insertion direction, wherein the shutter is configured to rotate about the rotational axis to move between the open position and the closed position; and
   an actuator for actuating the mechanism to move the shutter between the open position and the closed position; wherein the method comprises the steps of:
     controlling the actuator to actuate the mechanism to move the shutter in the open position;
     placing the biological sample on the test strip;
     inserting the test strip into the test strip port such that the test strip passes through the test strip opening and into the test strip mount;
     analyzing the test strip with the analytical unit to perform the measurement;
     removing the test strip from the medical instrument;
     controlling the actuator to actuate the mechanism to move the shutter in the closed position; and
     cleaning the exterior surface of the medical instrument.

2. A medical instrument, wherein the medical instrument is an analyzer for performing a measurement on a biological sample using a test strip, wherein the medical instrument comprises:

a housing with an exterior surface, wherein the housing comprises an interior surface surrounding an interior volume;

an analytical unit for analyzing the test strip, wherein the analytical unit is within the interior volume, wherein the analytical unit comprises a test strip mount configured for receiving the test strip to perform the measurement;

a test strip port between the exterior surface and the interior surface, wherein the test strip port is configured for receiving the test strip, wherein the test strip port is aligned with the test strip mount along an insertion direction;

a shutter for sealing the test strip port, wherein the shutter is configured for being in an open position and a closed position, wherein the shutter is within the interior volume, wherein the shutter is configured for sealing the test strip port when in the closed position, wherein the shutter comprises a test strip opening, wherein the test strip opening is aligned with the test strip port and the test strip mount when the shutter is in the open position, wherein the shutter has a first sealing surface, wherein the test strip port has a second sealing surface, wherein the first sealing surface and the second sealing surface are configured to mate in the closed position, wherein the shutter comprises a shutter mechanism for moving the shutter between the open position and the closed position, wherein moving the shutter between the closed position and the open position comprises a rotation of the shutter parallel to the insertion direction, wherein the shutter mechanism comprises a shutter shaft fixed to the shutter, wherein the shutter shaft is configured for rotating about a rotational axis, wherein the rotational axis is parallel to the insertion direction, wherein the shutter is configured to rotate about the rotational axis to move between the open position and the closed position; and an actuator for actuating the mechanism to move the shutter between the open position and the closed position.

3. The medical instrument of claim 2, wherein the shutter shaft has a fixed position along the rotational axis.

4. The medical instrument of claim 2, the shutter shaft is configured for translational motion along the rotational axis, wherein the shutter further comprises an actuator shaft configured for rotational motion along a driving axis, wherein the actuator shaft is rotationally connected to the actuator, wherein the driving axis is parallel to the rotational axis, wherein the shutter mechanism is configured such that rotational motion of the driving axis causes rotational motion of the actuator shaft about the rotational axis, wherein the shutter mechanism is further configured such that rotational motion of the driving axis causes translational motion of the actuator shaft along the rotational axis.

5. The medical instrument of claim 4, wherein the driving axis is coaxial with the rotational axis, wherein the shutter mechanism comprises a bearing sleeve for receiving the actuator shaft and the shutter shaft, wherein the shutter mechanism comprises a guiding pin connected to the shutter shaft, wherein the bearing sleeve is connected to the housing, wherein the bearing sleeve comprises a guideway for guiding the guiding pin to control the rate of translational motion of the shutter shaft relative to the rotational motion of the shutter shaft.

6. The medical instrument of claim 3, wherein the shutter mechanism further comprises an elastic element for returning the shutter into the open position or into the closed position.

7. The medical instrument of claim 2, wherein the actuator is a rotational motor.

8. The medical instrument of claim 2, wherein the shutter shaft is configured for translational motion along the rotational axis, wherein the shutter further comprises an actuator shaft configured for translational motion along a driving axis, wherein the actuator shaft is configured for translationally driving the shutter shaft along the rotational axis, wherein the driving axis is parallel to the rotational axis, wherein the shutter mechanism is configured such that translational motion of the driving axis causes rotational motion of the actuator shaft about the rotational axis, wherein the shutter mechanism is further configured such that translational motion of the driving axis causes rotational motion of the actuator shaft along the rotational axis.

9. The medical instrument of claim 8, wherein the driving axis is coaxial with the rotational axis, wherein the shutter mechanism comprises a bearing sleeve for receiving the actuator shaft and the shutter shaft, wherein the shutter mechanism comprises a guiding pin connected to the shutter shaft, wherein the bearing sleeve is connected to the housing, wherein the bearing sleeve comprises a guideway for guiding the guiding pin to control the rate of rotational motion of the shutter shaft relative to translational motion of the shutter shaft.

10. The medical instrument of claim 2, wherein the actuator is a linear actuator.

11. The medical instrument of claim 2, wherein the first sealing surface is formed from a gasket.

12. The medical instrument of claim 2, wherein the analytical unit is any one of the following: an optical test strip analyzer, an electrochemical test strip analyzer, and combinations thereof.

13. The medical instrument of claim 2, wherein the actuator comprises a motor, wherein the medical instrument further comprises a memory for storing machine executable instructions, wherein the medical instrument further comprises a processor for controlling the medical instrument, wherein execution of the machine executable instructions causes the processor to:

control the motor to actuate the shutter mechanism to move the shutter in the open position;

analyze the test strip with the analytical unit to perform the measurement when the test strip is inserted into the test strip mount and the biological sample is placed on the test strip; and control the motor to actuate the shutter mechanism to move the shutter in the closed position when the test strip is removed from the test strip mount and the test strip port.

14. The medical instrument of claim 13, wherein the medical instrument further comprises a user interface for receiving user input that indicates that the medical instrument has been cleaned, wherein execution of the machine executable instructions further cause the processor to control the motor to actuate the mechanism to move the shutter in the open position after receiving the user input.

15. The medical instrument of claim 2, wherein the second sealing surface is within the interior volume.

16. The medical instrument of claim 2, wherein the 30 second sealing surface is on the on the interior surface.

17. The medical instrument of claim 2, wherein in the open position the first sealing surface is within the interior volume.

18. The medical instrument of claim 2, wherein the first sealing surface and the second sealing surface form the seal within the interior volume when the shutter is in the dosed position.

19. The medical instrument of claim 2, wherein the test strip port is an opening in the housing.

20. The medical instrument of claim 19, wherein the test strip port contacts the interior surface and the exterior surface.

\* \* \* \* \*